US010254205B2

(12) United States Patent
Vernede et al.

(10) Patent No.: US 10,254,205 B2
(45) Date of Patent: Apr. 9, 2019

(54) METHOD FOR CHARACTERIZING THE CRACKING MECHANISM OF A MATERIAL FROM THE FRACTURE SURFACE THEREOF

(71) Applicants: UNIVERSITE PIERRE ET MARIE CURIE (PARIS 6), Paris (FR); CENTRE NATIONAL DE LA RECHERCHE SCIENTIFIQUE, Paris (FR); Stephane Vernede, Shanghai (CN)

(72) Inventors: Stephane Vernede, Shanghai (CN); Laurent Ponson, Paris (FR)

(73) Assignees: SORBONNE UNIVERSITE, Paris (FR); CENTRE NATIONAL DE LA RECHERCHER SCIENTIFIQUE (CNRS), Paris (FR); Stephane Vernede, Shanghai (CN)

( * ) Notice: Subject to any disclaimer, the term of this patent is extended or adjusted under 35 U.S.C. 154(b) by 39 days.

(21) Appl. No.: 15/514,916

(22) PCT Filed: Sep. 30, 2015

(86) PCT No.: PCT/EP2015/072611
§ 371 (c)(1),
(2) Date: Mar. 28, 2017

(87) PCT Pub. No.: WO2016/050871
PCT Pub. Date: Apr. 7, 2016

(65) Prior Publication Data
US 2017/0261414 A1 Sep. 14, 2017

(30) Foreign Application Priority Data
Oct. 3, 2014 (FR) ...................................... 14 59525

(51) Int. Cl.
*G01N 3/06* (2006.01)
*G01B 21/30* (2006.01)
(Continued)

(52) U.S. Cl.
CPC ..... *G01N 3/068* (2013.01); *G01N 2203/0066* (2013.01); *G01N 2203/0212* (2013.01)

(58) Field of Classification Search
CPC ........... G01N 3/068; G01N 2203/0066; G01N 2203/0212
(Continued)

(56) References Cited

U.S. PATENT DOCUMENTS 8,229,681 B2 * 7/2012 Minnaar ................. G01N 3/08
702/187
2007/0213942 A1 9/2007 Ponson et al.
2013/0013223 A1 1/2013 Hirano et al.

FOREIGN PATENT DOCUMENTS

FR 2 892 811 A1 5/2007
JP 11-101625 A 4/1999

OTHER PUBLICATIONS

International Search Report issued in Application No. PCT/EP2015/072611, dated Nov. 2, 2015.
(Continued)

Primary Examiner — John H Le
(74) Attorney, Agent, or Firm — Young & Thompson (57) ABSTRACT

The disclosed method includes, from a topographic map showing, for a set of points {x} located in a midplane of the fracture surface, a height of the fracture surface h relative to the midplane: a step of determining, for each point x on the topographic map, a quantity $\omega_\varepsilon$ representative of an average difference in height$)_{I\delta xI \le \varepsilon}$ between the height h of the fracture surface at point x in question and the height h of the fracture surface at one or more points {x+δx} located inside a circle of radius ε centered on point x in question, a step of determining, according to a test distance δr, a spatial correlation function Cε representing a spatial correlation between points {x} and points {x+δx} such as IδxI=δr, and a step of determining a correlation length ξ from the spatial correlation function Cε.

19 Claims, 3 Drawing Sheets

(51) Int. Cl.
*G01B 21/20* (2006.01)
*G01B 5/30* (2006.01)
*G06F 19/00* (2018.01)

(58) Field of Classification Search
USPC .................................... 702/35, 36, 168, 179
See application file for complete search history.

(56) References Cited

OTHER PUBLICATIONS

French Search Report issued in Application No. FR 1459525, dated Jun. 8, 2015.
Bouchaud, E., "Scaling Properties of Cracks," Journal of Physics: Condensed Matter, vol. 9, No. 21, dated May 26, 1997, pp. 4319-4344.
Uchida, Y., et al., "Relationship Between Fatigue Striation Height and Stress Ratio," Journal of Materials Science, vol. 34, No. 10, May 1, 1999, pp. 2411-2419.
Guerra, C., et al., "Understanding Fast Macroscale Fracture from Microcrack Post Mortem Patterns," PNAS, vol. 109, 2012, pp. 390-394.
Barrenblatt, G., "The Mathematical Theory of Equilibrium Cracks Formed in Brittle Fracture," Ad. Appl. Mech., 1965, 115 pages.
Charles, R., "Static Fatigue of Glass," Journal of Applied Physics, vol. 29, No. 11, Nov. 1958, pp. 1549-1553.
Lawn, B., "Fracture of Brittle Solids—Second Edition," Cambridge University Press, 1993, 399 pages.

\* cited by examiner

METHOD FOR CHARACTERIZING THE CRACKING MECHANISM OF A MATERIAL FROM THE FRACTURE SURFACE THEREOF

TECHNICAL FIELD

The invention relates to the field of the characterization of materials, and more particularly, to the field of fractographic analysis of the fracture of a structure, from at least one of the fracture surfaces thereof. It applies particularly to determining a characteristic length of the damage processes involved in the cracking of the structure, allowing the toughness and the fracture energy of the material constituting the structure to be determined, and the cause of a fracture to be determined. More specifically, the invention relates to a method for the characterization of a fracture surface in a solid structure having undergone cracking, the method relying on statistical analysis of the data of a topographical map representing, for a set of points situated in a mean plane of the fracture surface, the height of the fracture surface with respect to this mean plane.

STATE OF THE PRIOR ART

Study of the morphology of a fracture surface in a part allows many items of information to be obtained on the properties of the material of this part, and on the cracking mechanism that resulted in the fracture of the part. In particular, for a wide variety of heterogeneous materials, it has been concluded that the fracture surfaces exhibit universal properties, although the fracture mechanisms on a microscopic scale are very different from one material to another (Bouchaud, E.: Scaling properties of cracks, J. Phys. Condens. Matter 9, 4319-4344, 1997). Many experimental studies have in fact suggested that the fracture surfaces are self-affine over a wide range of length scales, i.e., along a given direction of the surface, the spatial variation of the height-height correlation function develops with respect to the x-axis according to a power law. Thus, by denoting the height-height correlation function along a given direction as follows:

$$\Delta h(\Delta r) = \langle (h(r+\Delta r)-h(r))^2 \rangle_r^{1/2}$$

the spatial variation of this function can be written:

$$\Delta h/l = (\Delta r/l)^H$$

where h is the height at the x-axis r, $\Delta h$ is the mean height difference between two points $\Delta r$ apart, the exponent H is the roughness exponent, also called Hurst exponent, and l is the topothesy or length scale for which $\Delta h(\Delta r=l)=l$. Several studies have concluded that the variable H must be universal and isotropic, substantially equal to 0.75.

In patent application FR 2 892 811, it was described that the Hurst exponent is in fact anisotropic. More particularly, in the direction of propagation of a crack, it has a value $\beta$ substantially equal to 0.60, and in the direction parallel to the crack front, a variable $\xi$ substantially equal to 0.75. The value of the Hurst exponent is thus less in the direction of propagation of the crack. This anisotropy thus makes it possible to recreate the direction of propagation of the crack.

Patent application US 2013/013223 describes a method for determining mechanical properties of a structure from an analysis of its fracture surfaces. More specifically, the method is based on a measurement by stereography of a density of lines of striation. These lines of striation are patterns specific to the mode of fracture by fatigue, following the application of a large number of loading and unloading cycles. Each line of striation corresponds to a relatively significant variation in the height of the points on a fracture surface. The inventors propose relationships between the density of the lines of striation and the mechanical properties of the material characterizing its fatigue resistance. In particular, the density of the striation lines is linked to the variation $\Delta K$ in the intensity factor of the stresses imposed during a loading and unloading cycle. Due to the nature of the data extracted on the fracture surfaces, this method applies only in the context of a fatigue fracture. Furthermore, determining lines of striation involves setting a threshold for differentiating, on the fracture surfaces, steps having a greater amplitude than the other steps. This threshold must be set with particular care in order to obtain reliable results. Finally, the number of lines of striations on a fracture surface is relatively small, typically of the order of approximately twenty lines. Thus the method is based on a small amount of information, which prevents the processing of fracture surfaces in different zones, and limits the accuracy of the results.

Among the techniques known from the state of the art, none makes it possible to deduce the dimension of the damage zone from the morphological analysis of the fracture surface. This damage zone corresponds to the zone at the cracking point where the dissipative mechanisms of cavitations and microcracking take place. The dimension of the damage zone is linked to the fracture energy of the material, and thus to its toughness. By toughness is meant the capacity of a material to resist the propagation of a crack.

Sophisticated imaging techniques make it possible to observe the process of cracking while it is taking place. However, due to the rapidity of the process, and the dimensions involved, in practice it is very difficult to observe and quantify this process. Furthermore, anticipating cracking, with regard to its location and the moment at which it takes place, is rarely possible. This is particularly the case when it is sought to analyze the origin of the facture of a part from an industrial machine or an aircraft, for example, after it has suffered an accident.

There is therefore a need to provide a method making it possible to determine, from analysis of the fracture surface of a part, at least one item of data relating to the fracture mechanisms of the material from which the part is made, or data relating to its strength. These items of information could be used in order to determine, post mortem, during an analysis phase, the conditions and causes of the fracture of a part. It should be noted that determining data relating to the mode of fracture of a material and its strength, via analysis of the fracture surface, makes it possible to gain information on the fracture of the material at the local level, at the same place where the part fractured, and at different sites on the fractured surface.

DISCLOSURE OF THE INVENTION

A first purpose of the invention is thus to provide a method for the characterization of a fracture surface of a solid structure, making it possible to determine a characteristic dimension of the damage zone.

A further purpose of the invention is to provide information on the cracking process that led to fracturing of the structure. This information relates for example to the shape and/or the length of the microcracks, their density or also the cracking velocity.

Yet a further purpose of the invention is to allow the post mortem determination of information relating to the cracking process after this process is completely finished. In practice, this aim is achieved by analyzing the fracture surface formed on the structure.

The invention will be better understood after consideration of the following few points. The cracking process in a structure develops by the formation of microcavities and microcracks which, by joining together, form a main crack, indicated by the fracture surface. This process of coalescence of microcracks/microcavities leaves marks on the fracture surface which adopt the form of cliffs, i.e. zones the local slope of which is particularly steep. As described in C. Guerra, J. Scheibert, D. Bonamy and D. Dalmas: "Understanding fast macroscale fracture from microcrack post mortem patterns", *PNAS* 109, 390-394 (2012), these patterns are explained by the fact that the different microcracks/microcavities develop in different geometrical planes, and thus give rise to sudden changes of levels or rapid height variations when they meet during the development of the fracture process. At a given moment of the cracking process, all the mechanisms of formation and coalescence of microcavities and microcracks occur in a delimited zone, called damage zone, situated around the crack point. The invention is based on the principle according to which the dimension of the damage zone is given by the correlation length of the network of cliffs present on the fracture surface. One of the applications of the invention is thus determining this dimension from analysis of the fracture surfaces.

More specifically, the invention relates to a method for the characterization, in a solid structure that has suffered cracking, of a fracture surface of this structure resulting from the cracking. The method comprises, from a topographical map representing, for a set of points $\{x\}$ situated in a mean plane of the fracture surface, a height $h(x)$ of the fracture surface with respect to the mean plane:

a step of determining, for each point x of the topographical map, a variable $\omega_\in(x)$ representative of an average height difference $\langle \delta h(x, \delta x) \rangle_{\delta x|\leq \in}$ between, on the one hand, the height $h(x)$ of the fracture surface at the point x in question and, on the other hand, the height $h(x+\delta x)$ of the fracture surface at one or more points $\{x+\delta x\}$ situated within a circle formed in the mean plane, of radius $\in$, and centred on the point x in question.

The set of variables $\omega_\in(x)$ defines a function over the set of points $\{x\}$.

The characterization method according to the invention can include the step of acquiring the topographical map. This acquisition step is then carried out prior to the step of determining the $\omega_\in(x)$ variables, and the topographical map obtained is used for this step of determining the $\omega_\in(x)$ variables.

In the present application, by "structure" is meant either a single part, or an integral assembly of several parts, for example welded or bonded together. The material of each part may be homogeneous or not. Furthermore, by "fracture surface" of the structure is meant the zone of this surface for which the topographical map has been prepared. In practice, this zone can cover the entire fracture surface of the structure, or only a portion. The mean plane of the fracture surface is then the mean plane of this zone.

The topographical map of the fracture surface gives, for a set of points $\{x(x; y)\}$ belonging to the mean plane, a height value $h(x)$ of the fracture surface with respect to the mean plane at each of these points. The points x are defined with respect to a frame of reference of the mean plane comprising an axis X, and an axis Y, not collinear with X. According to a first embodiment of the invention, the topographical map is two-dimensional. In other words, the points x are distributed in the mean plane in two non-parallel directions, for example axes X and Y. The points x are preferably distributed on the mean plane according to a regular matrix. In this case, the spatial resolution of the topographical map along the axis X is denoted dx, and the spatial resolution along the axis Y is denoted dy. These resolutions can be equal. The height $h(x)$ is defined along an axis Z that is non collinear with the axes X and Y. This axis is for example orthogonal to axes X and Y. The resolution dh of the topographical map along axis Z depends on the acquisition technique. In general, the resolutions dx, dy and dh must be adapted to the material of the part to be analyzed. More particularly, these resolutions must be determined so that the topographical map shows the roughness of the fracture surface at the scale of the damage. If $L_c$ is the enlargement of the damage zone, $dx \ll L_c$ and $dy \ll L_c$ will be chosen. By way of illustration, for a metallic material, the resolutions will advantageously be chosen close to one hundredth, or even one thousandth of the average size of the particles. For a wood material, the resolutions can be substantially less than the size of the cells, and for concrete, at that of the sand grains. In general, it will be preferable to choose a resolution that is smaller than the size of the largest microstructurel objects characterizing the material (for example, particle, cell, etc.) The technique for acquiring the topographical map depends on the material or materials of the structure to be analyzed. This is for example a mechanical profilometry, optical profilometry or microscopy technique.

According to a second embodiment of the invention, the topographical map is one-dimensional. The points x are then distributed in the mean plane on a straight line belonging to this plane. Conventionally, this is taken to be the straight line X. The points x can be distributed substantially equidistantly on the straight line, i.e. distributed with the spatial resolution dx.

The circles of radius $\in$, centred on the points x define a neighbourhood of these points. The points $\{x+\delta x\}$ can be chosen anywhere in this neighbourhood. In particular, they can be chosen on a closed curve to surrounding the point x in question. The closed curve is for example an ellipse, a circle, or a polygon, in particular a rectangle or a square. Preferably, the closed curve is a regular polygon or is substantially a circle. The points $\{x+\delta x\}$ in question are preferably distributed substantially equidistantly on the closed curve, so that they are representative of the "environment" of the point x in question. In the case of a one-dimensional topographical map, the circles of radius $\in$ in fact define a range of lengths centred on the point x in question.

According to a particular embodiment, the radius $\in$ of the circle is substantially comprised between approximately one times a spatial resolution of the topographical map in the mean plane and approximately ten times this spatial resolution. The spatial resolution in question is for example the spatial resolution dx, the spatial resolution dy, or an average of the spatial resolutions dx and dy. The radius $\in$ is advantageously equal to the largest of the two spatial resolutions dx and dy.

Due to their definition, the points $x+\delta x$ do not necessarily correspond to points x of the topographical map. Thus, the height $h(x+\delta x)$ of a point $x+\delta x$ can be determined either by considering the height of the point of the topographical map situated closest to this point, or by calculating the height of this point, for example based on an average of the heights of the adjacent points.

The variable $\omega_\in(x)$ is representative of the average height difference $\langle \delta h(x, \delta x)\rangle_{|\delta x|\leq\in}$ between the height $h(x)$ of the fracture surface at the point x in question, and the height $h(x+\delta x)$ of the fracture surface at one or more points $\{x+\delta x\}$ situated within (in particular on the perimeter of) a circle of radius $\in$, the circle belonging to the mean plane and being centred on the point x in question. In other words, the variable $\omega_\in(x)$ is representative of an average intensity of the height variations in the neighbourhood of the point x in question. In the case of a one-dimensional topographical map, the variable $\omega_\in(x)$ is representative, for each point x of the topographical map, of an average height difference $\langle \delta h(x, \delta x)\rangle_{\delta x|\leq\in}$ between, on the one hand, the height $h(x)$ of the fracture surface at the point x in question, and, on the other hand, the height $h(x+\delta x)$ of the fracture surface at one or more points $\{x+\delta x\}$ situated on each side of the point x in question, at a distance less than or equal to the radius $\in$. The variable $\omega_\in(x)$ is called "representative" of an average height difference in order to indicate that it is determined from this average height difference according to a predetermined relationship. This relationship can define the variable $\omega_\in(x)$ as being equal to the average height difference. It can also comprise the multiplication of the average height difference by a constant, or the addition of a constant. In other words, the variable $\omega_\in(x)$ is determined by an affine function taking as variable the average height difference. Inasmuch as the variable $\omega_\in(x)$ is representative of an average relating to a set of points taken within a circle, it gives reliable information on the presence of "cliffs" in the neighbourhood of this point. Over the set of points $\{x\}$, the variable $\omega_\in(x)$ defines a function or a field of height differences. This function $\omega_\in(x)$ has the advantage in particular of being only slightly impacted by any measurement artefacts. The function $\omega_\in(x)$ also makes it possible to produce an item of information on the spatial distribution of the height variations of greatest amplitude, and therefore on the shape and dimension of the microcracks and the microcavities formed in the damage zone.

According to a first embodiment, the variable $\omega_\in(x)$ is representative, for each point x of the topographical map, of an average height difference $\langle \delta h(x, \delta x)\rangle_{|\delta x|\sim\in}$ between the height $h(x)$ of the fracture surface at the point x in question, and the height $h(x+\delta x)$ of the fracture surface at one or more points $\{x+\delta x\}$ situated substantially on the perimeter of the circle of radius $\in$ centred on the point x in question. In other words, the variable $\omega_\in(x)$ is defined by the relationship:

$$\omega_\in(x)=f(\langle \delta h(x,\delta x)\rangle_{\delta x|\sim\in})$$

where the function $a\to f(a)$ is an affine function, where the quantity $\delta h(x, \delta x)$ defines the height difference $h(x+\delta x)-h(x)$, where the sign $\sim$ indicates a substantially equal quantity, and where the operator $\langle \delta h(x, \delta x)\rangle_{|\delta x|\sim\in}$ returns an average value of the height differences for the set of pairs of points $\{x; x+\delta x\}$ of the topographical map such that the distance $|\delta x|$ is substantially equal to the radius $\in$. The points $\{x+\delta x\}$ can be distributed equidistantly on the perimeter of the circle. The function $\omega_\in(x)$ is then isotropic.

According to a second embodiment, the variable $\omega_\in(x)$ is determined, for each point x of the topographical map, by the relationship:

$$\omega_\epsilon(x) = f\left(\frac{1}{2}\log(\langle \delta h^2(x, \delta x)\rangle_{|\delta x|\sim\epsilon})\right)$$

where the function $a\to f(a)$ is an affine function, where the quantity $\delta h(x, \delta x)$ defines the height difference $h(x+\delta x)-h$ (x), where the sign $\sim$ indicates a substantially equal quantity, where the operator $\langle \delta h(x, \delta x)\rangle_{|\delta x|\sim\in}$ returns an average value of the height differences for the set of pairs of points $\{x; x+\delta x\}$ of the topographical map such that the distance $|\delta x|$ is substantially equal to the radius $\in$, and where the function $a\to\log(a)$ is a logarithmic function. This can be in particular the decimal logarithm. This variant embodiment has the advantage of smoothing the height differences and making the indicator formed by the variable $\omega_\in(x)$ more robust. Squaring the variable $\delta h(x, \delta x)$ makes it possible to obtain a positive value for the height difference. It is particularly useful in the absence of normalization of heights $h(x)$.

According to a third embodiment, the variable $\omega_\in(x)$ is determined, for each point x of the topographical map, by the relationship:

$$\omega_\in(x)=f(\text{sign}(\langle \delta h(x,\delta x)\rangle_{|\delta x|\sim\in}))$$

in which the function $a\to\text{sign}(a)$ is a sign function taking the value 1 if a is strictly positive, −1 if a is strictly negative, and 0 if a is zero, where the quantity $\delta h(x, \delta x)$ defines the height difference $h(x+\delta x)-h(x)$, where the sign $\sim$ indicates a quantity that is substantially equal, and where the operator $\langle \delta h(x, \delta x)\rangle_{|\delta x|\sim\in}$ returns an average value for the height differences for the set of pairs of points $\{x; x+\delta x\}$ of the topographical map such that the length $|\delta x|$ is substantially equal to the radius $\in$.

In each of the variant embodiments, the relationship defining the variable $\omega_\in(x)$ can comprise a real constant $\Omega_\in$ determined so that an average of the function $\omega_\in(x)$ is substantially zero over the set of points $\{x\}$ of the topographical map. The real constant is then determined by the relationship:

$$\Omega_\in=\langle \omega_\in(x)\rangle_x.$$

The relationships defining the variable $\omega_\in(x)$ thus become respectively:

$$\omega_\epsilon(x) = \langle \delta h(x, \delta x)\rangle_{|\delta x|\sim\epsilon} - \Omega_\epsilon$$

$$\omega_\epsilon(x) = \frac{1}{2}\log(\langle \delta h^2(x, \delta x)\rangle_{|\delta x|\sim\epsilon}) - \Omega_\epsilon$$

$$\omega_\epsilon(x) = \text{sign}(\langle \delta h(x, \delta x)\rangle_{|\delta x|\sim\epsilon}) - \Omega_\epsilon$$

Regardless of the form of the function $\omega_\in(x)$, it is possible to study its autocorrelation as a function of a distance between pairs of points. The method according to the invention can thus comprise a step of determining, as a function of a test distance $\delta r$, a spatial correlation function $C_\in(\delta r)$ representative of a spatial correlation between the function $\omega_\in(x)$ determined for the set of points $\{x\}$, and the function $\omega_\in(x+\delta x)$ determined for the set of points $\{x+\delta x\}$ such that $|\delta x|=\delta r$. The spatial correlation function $C_\in(\delta r)$ is written:

$$C_\in(\delta r)=\langle \omega_\in(x)\cdot\omega_\in(x+\delta x)\rangle_{x,|\delta x|=\delta r}$$

The spatial correlation function $C_\in(\delta r)$ makes it possible to demonstrate a characteristic length, called correlation length $\xi$, delimiting two distance ranges. In the distance range $\delta r<\xi$, spatial correlation is observed between the functions $\omega_\in(x)$ and $\omega_\in(x+\delta x)$. This correlation is signified by the presence of height variations of the same amplitude over distances $\delta r$. In other words, it indicates the presence of cliffs the dimension of which is equal to $\delta r$. In the range of distances $\delta r>\xi$, the spatial correlation between the functions $\omega_\in(x)$ and $\omega_\in(x+\delta x)$ is zero, which signifies the absence of cliffs the dimension of which is greater than $\xi$.

The method according to the invention can thus comprise a step of determining the correlation length $\xi$ from the spatial correlation function $C_\in(\delta r)$, the correlation length $\xi$ being equal to the maximum distance $\delta r=|\delta x|$ separating pairs of points $\{x; x+\delta x\}$ beyond which the spatial correlation function $C_\in(\delta r)$ becomes substantially equal to $\Omega_\in^2$. For distances $\delta r<\xi$ The spatial correlation function $C_\in(\delta r)$ has values greater than $\Omega_\in^2$. When the relationship defining the variable $\omega_\in(x)$ is defined so that the function $\omega_\in(x)$ has an average of zero, the spatial correlation function $C_\in(\delta r)$ cancels out for distances $\delta r>\xi$.

As an alternative to an overall study of the autocorrelation of the function $\omega_\in(x)$, in all directions, it is possible to study its spatial autocorrelation in determined directions of the mean plane. Each direction, also called analysis direction, is referenced by an angle $\theta$ defined in the mean plane. The method can thus comprise a step of determining, as a function of a test distance $\delta r$ and a direction of analysis $\theta$, a spatial correlation function $C_{\in,\theta}(\delta r)$ representative of a spatial correlation between the function $\omega_\in(x)$ determined for the set of points $\{x\}$, and the function $\omega_\in(x+\delta x)$ determined for the set of points $\{x+\delta x\}$ situated at the distance $\delta r$ in the direction of analysis $\theta$.

A correlation length depending on the direction $\theta$, called correlation length $\xi_\theta$, can then by determined from the spatial correlation function $C_{\in,\theta}(\delta r)$. Similarly to the correlation length $\xi$, each correlation length $\xi_\theta$ is determined as being equal to the maximum distance $\delta r=|\delta x|$ separating pairs of points $\{x; x+\delta x\}$ beyond which the corresponding spatial correlation function $C_{\in,\theta}(\delta r)$ becomes substantially equal to $\Omega_\in^2$.

The inventors have been able to demonstrate that the variation in the correlation length $\xi_\theta$ as a function of the direction analyzed $\theta$ makes it possible to recreate the direction of propagation of the crack. In particular, the correlation length $\xi_\theta$ is maximum in the direction of propagation of the crack, and minimum in the direction orthogonal to the direction of propagation. The method according to the invention can thus comprise a supplementary step of determining the direction of propagation of the cracking from the correlation lengths $\xi_\theta$.

As the toughness $K_c$ of the material of a structure is linked to the size of the damage zone, and thus by the present invention, to the correlation length $\xi$, it is possible to determine this toughness $K_c$ from the measurement of $\xi$ carried out on the facture surfaces. By toughness is meant the capacity of a material to resist the propagation of a crack. According to a particular embodiment, the method then comprises a step of determining a toughness $K_c$ of the structure from the correlation length $\xi$. By way of example, for a material the damage zone of enlargement $L_c$ of which is described by a cohesive zone characterized by a breaking stress $\sigma_c$, the toughness $K_c$ follows the relationship:

$$K_c = \sqrt{\frac{8}{\pi}}\,\sigma_c\sqrt{L_c}$$

This relationship originates from the publication by G. I. Barrenblatt, "The mathematical theory of equilibrium of cracks in brittle solids", *Adv. Appl. Mech.* 7, 55 (1962). The correlation length determined from fracture surfaces via the present invention corresponds to the enlargement $L_c$ of the damage zone, and therefore the toughness of the material can be determined by means of the relationship:

$$K_c = \sqrt{\frac{8}{\pi}}\,\sigma_c\sqrt{\xi}$$

The breaking stress $\sigma_c$ of the material studied can then be determined independently, either by using conventional experimental methods, or by using the values provided in the literature. The breaking stress of a material is generally within the range $E/10<\sigma_c<E/5$ where E is the Young's modulus of the material.

According to another particular embodiment, the method comprises:

a step of determining, for each point x of the topographical map, a variable $\omega_\in(x)$ representative of an average height difference $\langle \delta h(x,\delta x)\rangle_{|\delta x|\sim\xi}$ between, on the one hand, the height $h(x)$ of the fracture surface at the point x in question and, on the other hand, the height $h(x+\delta x)$ of the fracture surface at one or more points $\{x+\delta x\}$ situated substantially on the perimeter of a circle of radius $\xi$ or $\xi_\theta$ centred on the point x in question, and a step of determining a variable $h_\xi$ corresponding to an average of the variables $\omega_\in(x)$ over the set of points $\{x\}$. This variable $h_\xi$ represents the enlargement of the damage zone in the direction orthogonal to the mean plane of the fracture surface.

The method can comprise, in addition:

a step of determining a toughness $K_c$ of the structure from the variable $h_\xi$.

The method can also comprise a step of determining the fracture energy $G_c$ of the material. In fact, the latter follows the relationship $G_c=K_c^2/E$ which makes it possible to link the fracture energy of the material with the correlation length extracted from the fracture surfaces via the relationship:

$$G_c = \frac{8}{\pi}\frac{\sigma_c^2}{E}\xi$$

Another application of measurement of the enlargement of the size of the damage zone based on the analysis of a fracture surface is the determination of the cracking velocity. This determination is based on the following observations. For a given material, broken at a given temperature, there is a monotone function $v=g(\xi)$ which links the correlation length $\xi$ to the cracking velocity v of the material: the larger the size of the damage zone $\xi$, the greater the cracking velocity also. This function can be determined in different ways. According to a first approach, the function $v=g(\xi)$ can be determined by conventional fracture tests using a traction machine. During these tests, cracking at a controlled velocity v is imposed on the material studied. The fracture surface obtained is then analyzed by using the method described in this patent, and the length $\xi$ is determined. This test is then carried out at different cracking velocities, so as to determine the relationship $v=g(\xi)$. This calibration can subsequently be used in a context where the cracking velocity is not known a priori and must be determined from the value of $\xi$ measured on the fracture surface.

Another approach intended to determine the function $v=g(\xi)$ consists of using an explicit expression of the function g which has either been determined beforehand by experiments, or established from modelling the cracking process. This modelling must also be adapted to the material studied. For example, the stress corrosion cracking that takes place in a large number of materials such as glasses or rocks results in a variation in the power-law crack velocity with the size of the damage zone, via Charles's phenomenological formula (R. J. Charles, "Static fatigue of glass", *J. Appl. Phys.* 29, 1554 (1958)):

$$v = A\xi^n$$

The constant A and the exponent n depend only on the material in question. It is possible in a large number of cases to use measurements taken by other authors and published in science journals in order to obtain the values of these two constants without the need to determine them by experiments. In other cases, it will be necessary to proceed to conventional fracture tests which will allow the determination of these two constants.

The method according to the invention can thus comprise, in addition:

a step of determining a cracking velocity v based, on the one hand, on the correlation length $\xi$ or on at least one correlation length $\xi_\theta$, and on the other hand, on a function $v=g(\xi)$ linking the correlation length $\xi$ or $\xi_\theta$ to the cracking velocity v.

A possible application of the measurement of the cracking velocity is the determination of the loading K applied during the fracture of the part analyzed. The greater the loading applied, the greater the cracking velocity. The relationship v(K) is known for a large number of materials (see for example B. Lawn, "Fracture of brittle solids", Cambridge Univ. Press, 1993). The loading applied during the fracture of the part represents a valuable item of information for understanding the conditions and the causes which have led to the failure of a structure.

Finally, it should be noted that the methods described above can be applied in two different ways:

(i) either the whole of the fracture surface is analyzed according to the procedure described above. This methodology makes it possible to determine an average correlation length $\xi$ over the whole of the fracture surface. From this value, it is then possible to determine the average toughness or the average cracking velocity over the whole of the part.

(ii) or the method for measuring $\xi$ is applied to different zones of the fracture surface. In fact, the method proposed produces results even from a relatively limited area of the fracture surface. The fracture surface studied can then be divided into various zones, and each zone studied individually. The topographical map can be determined by considering a single mean plane for the whole region of the fracture surface, or by considering a mean plane for each zone. Different steps of the method that are described above are then carried out for each of the zones of the fracture surface, so as to provide local information relating to the fracture surface. In the case in question, different correlation lengths $\xi$ or $\xi_\theta$ can be determined for the different zones. Reference may be made to a field of correlation lengths $\xi(x)$ or $\xi_\theta(x)$. Utilization of the relationships between $\xi$ and the toughness $K_c$ on the one hand, and $\xi$ and the cracking velocity v on the other hand, makes it possible to determine not just a value of $K_c$ or v, but their field $K_c(x)$ and $v(x)$ as a function of the position on the fracture surface. Similarly, it is possible to determine the local direction of cracking field. These fracture properties fields can prove to be valuable for determining the fracture behaviour of the material studied or the reasons for the fracture of a part, by recreating for example the weak point of the material, revealed either by the origin of the directions of propagation of the crack, or by a zone of lower toughness.

DESCRIPTION OF THE FIGURES

Other features and advantages of the invention will become apparent from reading the detailed description of non-limitative embodiments, together with the attached drawings in which.

DESCRIPTION OF EMBODIMENTS

As these embodiments are in no way limitative, variants of the invention can in particular be considered comprising only a selection of the characteristics described hereinafter, in isolation from the other characteristics described (even if this selection is isolated within a phrase containing other characteristics), if this selection of characteristics is sufficient to confer a technical advantage or to differentiate the invention with respect to the state of the prior art. This selection comprises at least one, preferably functional, characteristic without structural details, or with only a part of the structural details if this part alone is sufficient to confer a technical advantage or to differentiate the invention with respect to the state of the prior art.

Figure 1:
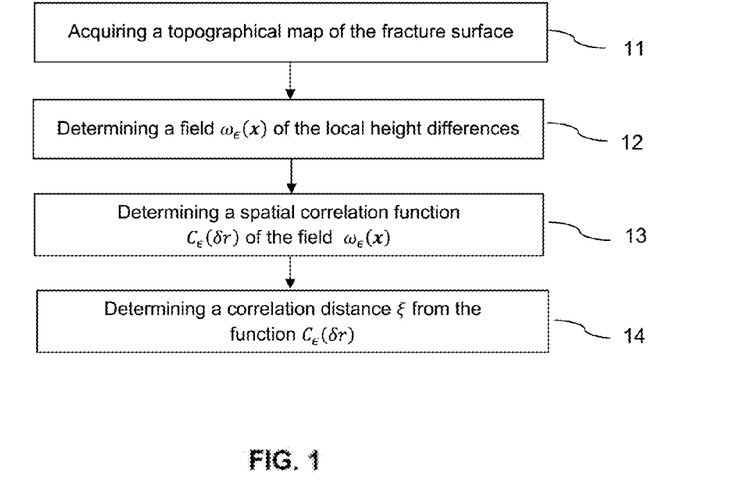
FIG. 1 shows an example of steps that can be implemented in the method for characterizing a fracture surface according to the invention.
Figure 2:
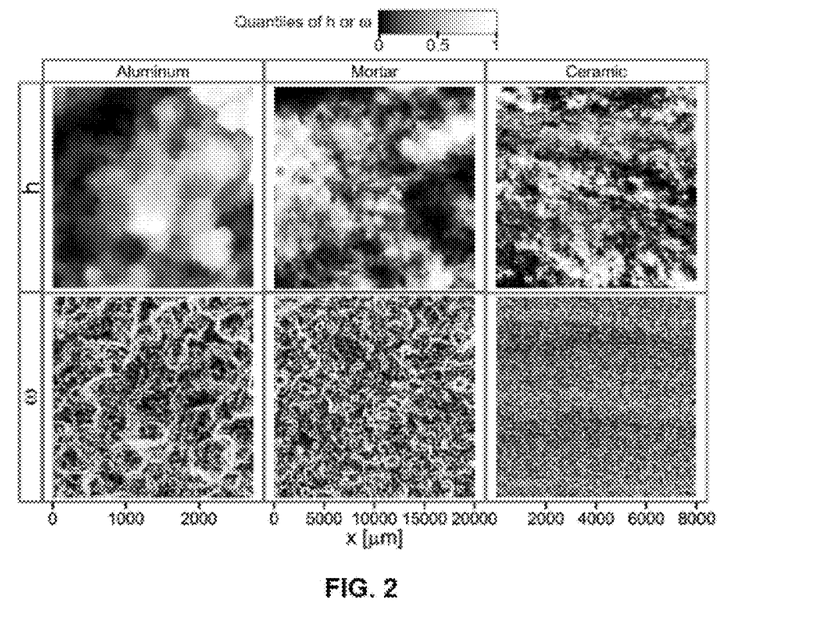
FIG. 2 shows, in its upper part, examples of topographical maps giving a height of a fracture surface with respect to a mean plane for different examples of materials and, in its lower part, fields $\omega_\in(x)$ having average height differences determined from these topographical maps.

FIG. 1 shows an example of steps that can be implemented in the method for characterizing a fracture surface according to the invention. In a first step 11 a topographical map is established for the fracture surface to be analysed. A topographical map represents, for a set of points {x} distributed regularly in a mean plane of the fracture surface in question, a height h(x) of the fracture surface with respect to this mean plane. Examples of topographical maps are illustrated in the upper part of FIG. 2 for fracture surfaces formed by cracking in parts constituted by different materials. The topographical map on the left illustrates the fracture surface of a part made from aluminium, the one in the middle illustrates the fracture surface of a part made from mortar, and the one on the right illustrates the fracture surface of a ceramic part. The points x or x(x; y) are defined with respect to a frame of reference of the mean plane comprising an axis X, corresponding in FIG. 2 to the horizontal axis, and an axis Y, corresponding to the vertical axis. The height h(x) is defined along an axis Z that is orthogonal to the axes X and Y. It is shown in FIG. 2 by a greyscale level; the lower the height, the darker the dot. In order to show these topographical maps and the fields $\omega_\in(x)$ in an instructive manner, the heights h(x) and $\omega_\in(x)$ have been normalized. All the heights h(x) are brought within a range of values comprised between 0 and 1, where the value 0 corresponds to the lowest height (situated below the mean plane) and the value 1 corresponds to the maximum height (situated above the mean plane). The same procedure is applied to the field $\omega_\in(x)$.

Each topographical map is established according to a suitable acquisition technique for the material in question. In the case in point, the topographical map in FIG. 2 for the part made from aluminium was established from a stereoscopic pair of images obtained by scanning electron microscopy, the topographical map for the part made from mortar was established by optical profilometry, and the topographical map for the ceramic part was established using mechanical profilometry. The spatial resolutions along the axes X and Y, marked dx and dy, are substantially equal and their values are 3 μm (micrometers), 50 μm and 8 μm, for the aluminium, the mortar and the ceramic, respectively. The accuracy of the measurements along the axis of the heights, i.e. along the axis Z, is equal to approximately 1 μm, 10 μm and 0.2 μm for the aluminium, the mortar and the ceramic, respectively.

In a second step 12 of the method according to the invention, a variable $\omega_\in(x)$ is determined for each point x of the topographical map. This variable $\omega_\in(x)$ is determined so as to be representative of an average height difference $\langle \delta h(x, \delta x)\rangle_{\delta x \leq \in}$ between, on the one hand, the height h(x) of the fracture surface at the point x in question and, on the other hand, the height h(x+δx) of the fracture surface at one or more points {x+δx} situated within a circle of radius ∈ centred on the point x in question. The length of the radius ∈ is preferably determined as a function of the spatial resolution of the topographical map, i.e. as a function of the scale of roughness of the fracture surface. The radius ∈ is for example comprised between approximately one times the spatial resolution of the topographical map and approximately ten times this resolution. Preferably, the radius ∈ is equal to the spatial resolution dx and/or dy. In the examples of FIG. 2, the length of the radius ∈ is chosen to be equal to the resolutions dx and dy of the topographical readings. Over the set of points {x}, the variables $\omega_\in(x)$ define a function. More specifically, they define a two-dimensional spatial function. This function is also called a field of the height differences, in particular when reference is made to its graphical representation.

The variable $\omega_\in(x)$ can be determined in different ways. According to a first embodiment, the variable $\omega_\in(x)$ is determined as being equal to the average height difference between the height h(x) of the fracture surface at the point x in question, and the height h(x+δx) of the fracture surface at one or more points {x+δx} situated substantially on the perimeter of the circle of radius ∈ centred on the point x in question. The variable $\omega_\in(x)$ is then defined by the relationship:

$$\omega_\in(x) = \langle \delta h(x,\delta x)\rangle_{|\delta x|=\in} \quad (1)$$

where δh(x, δx)=h(x+δx)−h(x) and where the operator $\langle \delta h(x, \delta x)\rangle_{|\delta x|=\in}$ returns an average value of the height differences for the set of pairs of points {x; x+δx} of the topographical map such that |δ|~∈.

According to a second variant embodiment, the variable $\omega_\in(x)$ is determined, for each point x of the topographical map, by the relationship:

$$\omega_\epsilon(x) = \frac{1}{2}\log(\langle \delta h^2(x, \delta x)\rangle_{|\delta x|\sim\epsilon}) \quad (2)$$

where the function a→log(a) is a logarithmic function, for example the decimal logarithm function.

According to a third embodiment, the variable $\omega_\in(x)$ is determined, for each point x of the topographical map, by the relationship:

$$\omega_\in(x)=\text{sign}(\langle \delta h(x,\delta x)\rangle_{|\delta x|\sim\in}) \quad (3)$$

in which the function a→sign(a) is a sign function taking the value 1 if a is strictly positive, −1 if a is strictly negative, and 0 if a is zero.

In each of the variant embodiments, the variable $\omega_\in(x)$ can be determined so that the function $\omega_\in(x)$ is substantially zero over the set of points {x} of the topographical map. A real constant $\Omega_\in$ is subtracted in the relationships (1), (2) and (3). This constant $\Omega_\in$ is defined from the corresponding variable $\omega_\in(x)$, by the relationship:

$$\Omega_\in = \langle \omega_\in(x)\rangle_x$$

The relationships (1), (2) and (3) then become:

$$\omega_\epsilon(x) = \langle \delta h(x, \delta x)\rangle_{|\delta x|\sim\epsilon} - \Omega_\epsilon \quad (1')$$

$$\omega_\epsilon(x) = \frac{1}{2}\log(\langle \delta h^2(x, \delta x)\rangle_{|\delta x|\sim\epsilon}) - \Omega_\epsilon \quad (2')$$

$$\omega_\epsilon(x) = \text{sign}(\langle \delta h(x, \delta x)\rangle_{|\delta x|\sim\epsilon}) - \Omega_\epsilon \quad (3')$$

The lower part of FIG. 2 illustrates the fields $\omega_\in(x)$ determined for the topographical maps of the upper part. Thus, from left to right, the fields $\omega_\in(x)$ are shown for the fracture surfaces of the aluminium, mortar and ceramic parts. These fields are defined in the same frame of reference as the topographical maps and are determined by the relationship (2'). In the representation in FIG. 2, the fields $\omega_\in(x)$ are also normalized by bringing each value for $\omega_\in(x)$ within a range of values comprised between 0 and 1, where the value 0 corresponds to the minimum height difference, and the value 1 corresponds to the maximum height difference. As can be seen in FIG. 2, the fields $\omega_\in(x)$ give information on the form and the dimension of the microcracks which resulted in the formation of the fracture surface. In particular, the lines the intensity of which is the clearest give the form of the microcracks at the moment of their coalescence with the other microcracks or with the main crack.

In a third step 13 of the method according to the invention, a spatial correlation function $C_\in(\delta r)$ is determined. This function is determined as a function of a test distance δr. This test distance δr preferably varies between the spatial resolution of the topographical map, and the largest dimension of the topographical map in the mean plane. It is representative of a spatial correlation between the function $\omega_\in(x)$ determined for the set of points {x}, and the function $\omega_\in(x+\delta x)$ determined for the set of points {x+δx} such that |δx|=δr. The spatial correlation function $C_\in(\delta r)$ is written:

$$C_\in(\delta r)=\langle \omega_\in(x)\cdot\omega_\in(x+\delta x)\rangle_{x,|\delta x|=\delta r} \quad (4)$$

Figure 3:
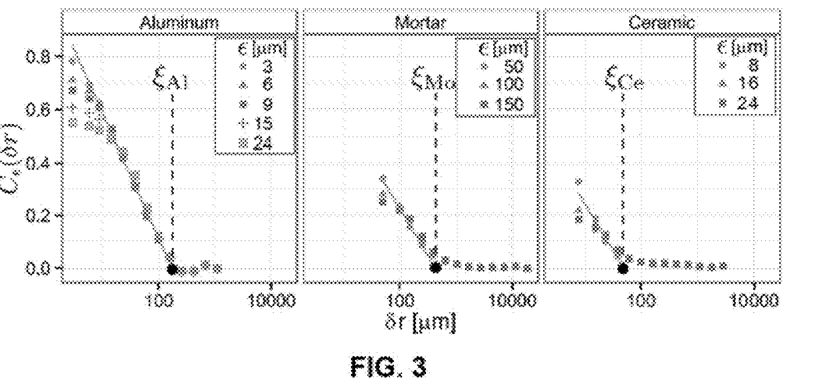
FIG. 3 shows, in the form of graphs, a spatial correlation function of the fields $\omega_\in(x)$ shown in FIG. 2.

FIG. 3 shows, in the form of graphs, the spatial correlation function $C_\in(\delta r)$ for the fracture surfaces of the aluminium, mortar and ceramic parts. The x-axis represents the test distance δr, and the y-axis represents the spatial correlation value for this distance. For each material, the correlation function $C_\in(\delta r)$ was marked for different lengths of radius ∈. In particular, for the aluminium part, the correlation function $C_\in(\delta r)$ was determined for radii of 3, 6, 9, 15, and 24 μm. The graphs demonstrate the fact that the correlation function $C_\in(\delta r)$ has a value of zero beyond a certain distance. This distance is called correlation length ξ. It provides information on the length of the damage zone of the cracking process. It should be noted that the correlation function $C_\in(\delta r)$ has a value of zero beyond the correlation length $\xi$ regardless of the length of the radius $\in$, while this length is less than the correlation length $\xi$. The graphs in FIG. 3 also show that the length of the radius $\in$ has a relatively limited influence on the form of the correlation function $C_\in(\delta r)$. This is particularly true for the distances $\delta r$ greater than a threshold distance. Thus, the choice of the length of the radius $\in$ used for determining the function $\omega_\in(x)$ has no critical influence on the remainder of the method, and in particular on the accuracy of the correlation length $\xi$.

Figure 4:
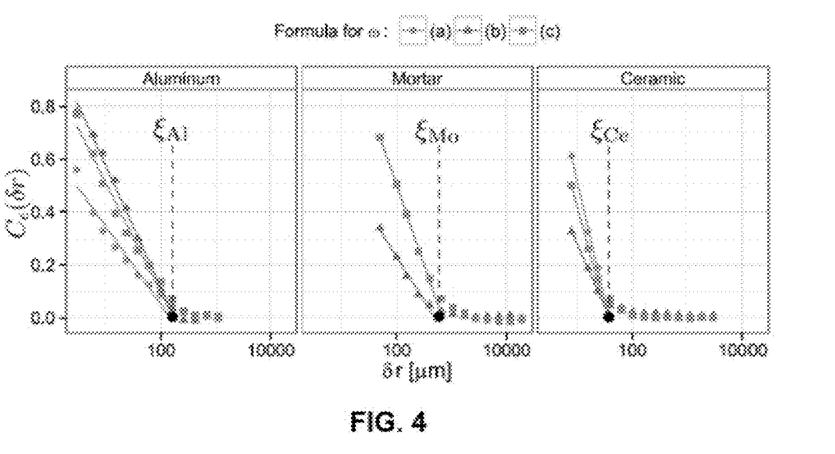
FIG. 4 shows, in the form of graphs, spatial correlation functions determined from different relationships for the fields $\omega_\in(x)$.

FIG. 4 shows different spatial correlation functions $C_\in(\delta r)$ for the fracture surfaces of the aluminium, mortar and ceramic parts. The x-axis represents the test distance $\delta r$, and the y-axis represents the spatial correlation value for this distance. For each material, the correlation function $C_\in(\delta r)$ was determined and plotted for different functions $\omega_\in(x)$, denoted (a), (b), and (c), and defined as follows:

$$\omega_\epsilon(x) = \frac{\langle \delta h(x, \delta x)\rangle_{|\delta x|=\epsilon} - \Omega_\epsilon}{\sigma_\epsilon} \quad (a)$$

$$\omega_\epsilon(x) = \frac{1}{2}\log(\langle \delta h^2(x, \delta x)\rangle_{|\delta x|=\epsilon}) - \Omega_\epsilon \quad (b)$$

$$\omega_\epsilon(x) = \langle \operatorname{sign}(\delta h(x, \delta x))\rangle_{|\delta x|=\epsilon} - \Omega_\epsilon \quad (c)$$

where the quantity $\sigma_\in$ denotes the standard deviation of the function $\omega_\in(x)$. In the function (a), division by $\sigma_\in$ allows the correlation function to be shown on one and the same graph as the correlation functions obtained with (b) and (c). It should be noted that the function (c) could have an alternative form, as follows:

$$\omega_\in(x) = \operatorname{sign}(\langle \delta h(x, \delta x)\rangle_{|\delta x|=\in}) - \Omega_\in$$

The method according to the invention comprises a fourth step 14, in which the correlation length $\xi$ is determined from the correlation function $C_\in(\delta r)$. This step can be carried out in different ways. It consists for example of determining the smallest value of $\delta r$ for which the value of the correlation function $C_\in(\delta r)$ is less than a predetermined threshold value. In another embodiment, this step is carried out by selecting a set of points the value of which is greater than a predetermined threshold, substantially equal to $\omega_\in^2 = \langle \omega_\in(x)\rangle_x^2$, by plotting a straight line passing as close as possible to the selected points, and by determining the distance $\delta r$ for which this straight line intersects the straight line of equation $C_\in(\delta r) = \Omega_\in^2$. FIG. 4 demonstrates the fact that the correlation length $\xi$ is relatively independent of the relationship chosen for the function $\omega_\in(x)$.

Figure 5:
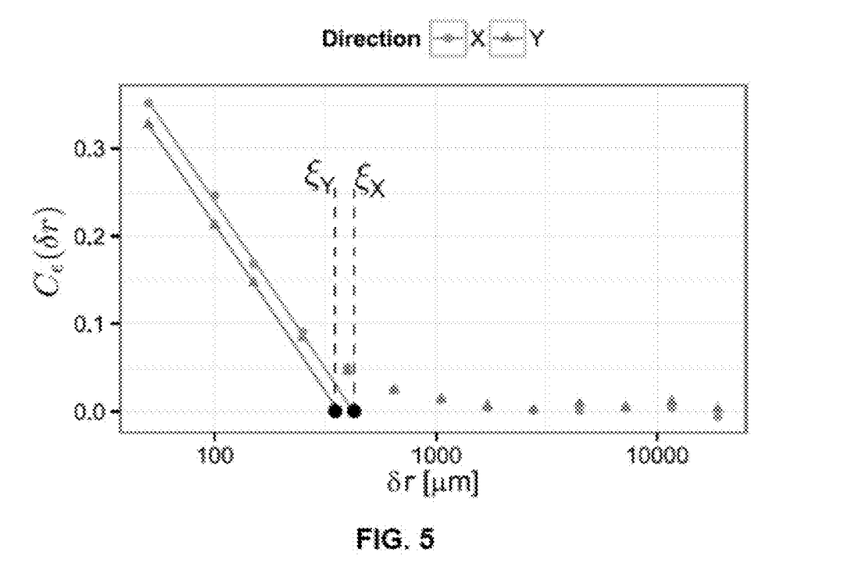
FIG. 5 shows a spatial correlation function determined for one and the same fracture surface in two different directions.

FIG. 5 represents a spatial correlation function determined in two different directions for a fracture surface on a part made from mortar. A first direction, denoted X, corresponds to the direction of propagation of the crack. A second direction, denoted Y, corresponds to a direction perpendicular to the direction of propagation, in the mean plane. As can be seen clearly in FIG. 5, the correlation length $\xi_X$ in direction X of propagation of the crack is greater than the correlation length $\xi_Y$ in the direction Y.

Figure 6:
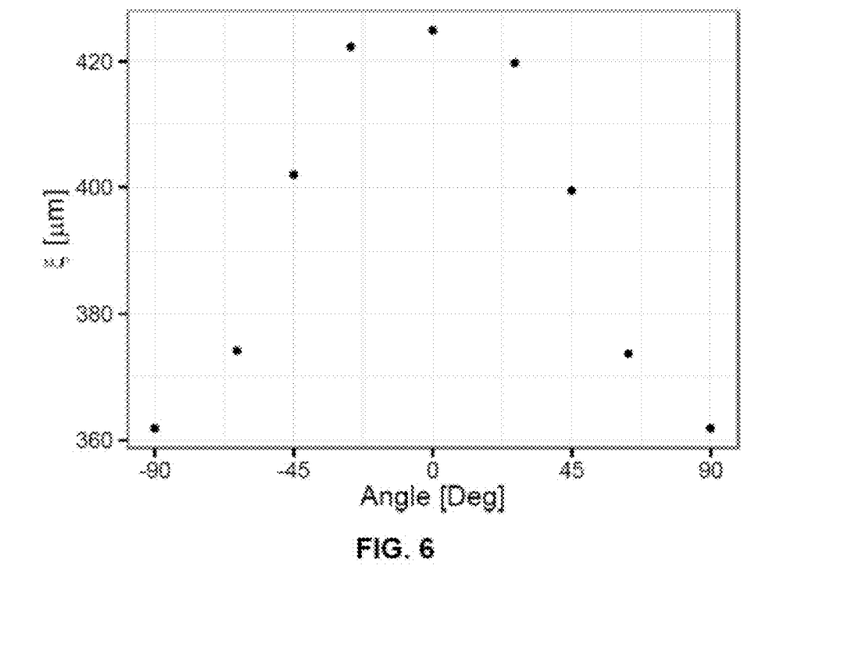
FIG. 6 shows the development of a correlation length as a function of a direction of the spatial correlation.

FIG. 6 shows more specifically the variation in the correlation length $\xi_\theta$ as a function of the spatial correlation direction. It can be noted that the correlation length $\xi_\theta$ passes through a maximum for an angle of zero degrees, corresponding to the direction of propagation of the crack.

The method according to the invention can comprise additional steps of determining mechanical properties of the material or materials of the structure from the function $\omega_\in(x)$, the correlation function $C_\in(\delta r)$ (or at least one function $C_{\in,\theta}(\delta r)$) and/or the correlation length $\xi$ (or at least one correlation length $\xi_\theta$).

The toughness $K_c$ of a material can in particular be determined from the correlation length $\xi$ or at least one correlation length $\xi_\theta$. By way of example, for a material the damage zone of enlargement $L_c$ of which is described by a cohesive zone characterized by a breaking stress $\sigma_c$, the toughness $K_c$ follows the relationship:

$$K_c = \sqrt{\frac{8}{\pi}}\, \sigma_c \sqrt{L_c}$$

This relationship originates from the publication G. I. Barrenblatt, "The mathematical theory of equilibrium of cracks in brittle solids", *Adv. Appl. Mech.* 7, 55 (1962). The correlation length $\xi$ determined from fracture surfaces according to the present invention gives the enlargement $L_c$ of the damage zone, and therefore the toughness of the material, through the relationship:

$$K_c = \sqrt{\frac{8}{\pi}}\, \sigma_c \sqrt{\xi}$$

The breaking stress $\sigma_c$ of the material studied can then be determined independently, either by using conventional experimental methods, or by using the values provided in the literature. The breaking stress of a material is generally within the range $E/10 < \sigma_c < E/5$ where E is the Young's modulus of the material.

The method can also comprise a step of determining the fracture energy $G_c$ of the material. In fact, the latter follows the relationship $G_c = K^2/E$ which makes it possible to link the fracture energy of the material with the correlation length extracted from the fracture surfaces via the relationship:

$$G_c = \frac{8}{\pi}\frac{\sigma_c^2}{E}\xi$$

Of course, the invention is not limited to the examples which have just been described and numerous adjustments can be made to these examples without exceeding the scope of the invention. In particular, the various characteristics, forms, variants and embodiments of the invention can be combined together in various combinations if they are not incompatible or mutually exclusive.

The invention claimed is:

1. Method for characterizing, in a solid structure having undergone cracking, a fracture surface of the structure resulting from the cracking, the method comprising:
   acquiring by an acquisition device, a topographical map representing, for a set of points $\{x\}$ situated in a mean plane of the fracture surface, a height $h(x)$ of the fracture surface with respect to the mean plane; and
   determining a variable $\omega_\in(x)$, for each point x of the topographical map, each variable $\omega_\in(x)$ representing an average height difference $\langle \delta h(x,\delta x)\rangle_{|\delta x|\leq \in}$ between the height $h(x)$ of the fracture surface at the point x in question and the height $h(x+\delta x)$ of the fracture surface at one or more points $\{x+\delta x\}$ situated within a circle formed in the mean plane, of radius $\in$, and centred on the point x in question, a set of the variables $\omega_\in(x)$ defining a function over the set of points {x}, wherein the variables $\omega_\in(x)$ provide information on the form and the dimension of microcracks having led to the cracking.

2. Method according to claim 1, wherein a relationship defining the variable $\omega_\in(x)$ comprises a real constant $\Omega_\in$ determined so that an average of the function $\omega_\in(x)$ is substantially zero over the set of points {x} of the topographical map.

3. Method according to claim 1, further comprising:
determining a spatial correlation function $C_\in(\delta r)$, as a function of a test distance $\delta r$, the spatial correlation function $C_\in(\delta r)$ representing a spatial correlation between the function $\omega_\in(x)$ determined for the set of points {x}, and the function $\omega_\in(x+\delta x)$ determined for the set of points {x+$\delta x$} such that $|\delta x|=\delta r$.

4. Method according to claim 3, further comprising:
determining a correlation length $\xi$ from the spatial correlation function $C_\in(\delta r)$, the correlation length $\xi$ being equal to the maximum distance $\delta r=|\delta x|$ separating pairs of points {x; x+$\delta x$} beyond which the spatial correlation function $C_\in(\delta r)$ becomes substantially equal to $\Omega_\in^2 = \langle \omega_\in(x) \rangle_x^2$.

5. Method according to claim 4, further comprising:
determining a toughness $K_c$ of the structure from the correlation length $\xi$ or at least one correlation length $\xi_\theta$.

6. Method according to claim 4, further comprising:
determining a cracking velocity v from the correlation length $\xi$ or at least one correlation length $\xi_\theta$, and on a function $v=g(\xi)$ linking the correlation length $\xi$ or $\xi_\theta$ to the cracking velocity v.

7. Method according to claim 4, further comprising:
determining a variable $\omega_\xi(x)$ for each point x of the topographical map, the variable $\omega_\xi(x)$ representing an average height difference $\langle \delta h(x,\delta x) \rangle_{|\delta x|\sim\xi}$ between the height h(x) of the fracture surface at the point x in question and the height h(x+$\delta x$) of the fracture surface at one or more points {x+$\delta x$} situated substantially on the perimeter of a circle of radius $\xi$ or $\xi_\theta$ centred on the point x in question, and
determining a variable $h_\xi$ corresponding to an average of the variables $\omega_\xi(x)$ over the set of points {x}.

8. Method according to claim 7, further comprising:
determining a toughness $K_c$ of the structure from the variable $h_\xi$.

9. Method according to claim 1, wherein the topographical map represents a height h(x) of the fracture surface with respect to the mean plane for a set of points {x} situated on a straight line belonging to the mean plane, the variable $\omega_\in(x)$ being representative, for each point x of the topographical map, of an average height difference $\langle \delta h(x, \delta x) \rangle_{|\delta x|\leq\in}$ between the height h(x) of the fracture surface at the point x in question and the height h(x+$\delta x$) of the fracture surface at one or more points {x+$\delta x$} situated on either side of the point x in question at a distance less than or equal to the radius $\in$.

10. Method according to claim 1, wherein the topographical map represents a height h(x) of the fracture surface with respect to the mean plane for a set of points {x} distributed in the mean plane in two non-parallel directions.

11. Method according to claim 10, further comprising:
determining a spatial correlation function $C_{\in,\theta}(\delta r)$ as a function of a test distance $\delta r$ and a direction of analysis $\theta$ in the mean plane, the spatial correlation function $C_{\in,\theta}(\delta r)$ representing a spatial correlation between the function $\omega_\in(x)$ determined for the set of points {x}, and the function $\omega_\in(x+\delta x)$ determined for the set of points {x+$\delta x$} situated at the distance $\delta r$ in the direction of analysis $\theta$.

12. Method according to claim 11, wherein the spatial correlation function $C_{\in,\theta}(\delta r)$ is determined for different directions of analysis $\theta$, the method further comprising:
determining a correlation length $\xi_\theta$ for each direction of analysis $\theta$ from the corresponding spatial correlation function $C_{\in,\theta}(\delta r)$, the correlation length $\xi_\theta$ being equal to the maximum distance $\delta r=|\delta x|$ separating pairs of points {x; x+$\delta x$} beyond which the spatial correlation function $C_{\in,\theta}(\delta r)$ becomes substantially equal to $\Omega_\in^2 = \langle \omega_\in(x) \rangle_x^2$.

13. Method according to claim 12, further comprising:
determining a direction of propagation of the cracking based on variations in the correlation length $\xi_\theta$ with the direction of analysis $\theta$.

14. Method according to claim 1, wherein the radius $\in$ of the circle is substantially comprised between one times a spatial resolution of the topographical map in the mean plane and approximately ten times this spatial resolution.

15. Method according to claim 1, wherein: the fracture surface is divided into several zones, the topographical map representing a height h(x) of the fracture surface with respect to a mean plane in each of the zones, said determining a variable $\omega_\in(x)$, said determining a spatial correlation function $C_\in(\delta r)$, and said determining a correlation length $\xi$ being carried out individually for each of the zones of the fracture surface, so as to provide local information relating to the fracture surface, and in particular a correlation lengths field $\xi(x)$ or $\xi_\theta(x)$, a toughness field $K_c(x)$, a cracking velocity field v(x), and a local direction of cracking field.

16. Method according to claim 1, wherein the variable $\omega_\in(x)$ is representative, for each point x of the topographical map, of an average height difference $\langle \delta h(x,\delta x) \rangle_{|\delta x|\leq\in}$ between, on the one hand, the height h(x) of the fracture surface at the point x in question, and, on the other hand, the height h(x+$\delta x$) of the fracture surface at one or more points {x+$\delta x$} situated on a closed curve surrounding the point x in question.

17. Method according to claim 1, wherein the variable $\omega_\in(x)$ is representative, for each point x of the topographical map, of an average height difference $\langle \delta h(x,\delta x) \rangle_{|\delta x|\sim\in}$ between the height h(x) of the fracture surface at the point x in question, and the height h(x+$\delta x$) of the fracture surface at one or more points {x+$\delta x$} situated substantially on the perimeter of the circle of radius $\in$ centred on the point x in question.

18. Method according to claim 1, wherein the variable $\omega_\in(x)$ is determined, for each point x of the topographical map, by the relationship:

$$\omega_\in(x) = f\left(\frac{1}{2}\log(\langle \delta h^2(x, \delta x) \rangle_{|\delta x|\sim\in})\right)$$

where the function $a \rightarrow f(a)$ is an affine function, where the function $a \rightarrow \log(a)$ is a logarithmic function, where the quantity $\delta h(x,\delta x)$ defines the height difference $h(x+\delta x)-h(x)$, where the sign ~ indicates a substantially equal quantity, and where the operator $\langle \delta h(x,\delta x) \rangle_{|\delta x|\sim\in}$ returns an average value of the height differences for the set of pairs of points $\{x;x+\delta x\}$ of the topographical map such that the distance $|\delta x|$ is substantially equal to the radius $\in$.

19. Method according to claim 1, wherein the variable $\omega_\in(x)$ is determined, for each point x of the topographical map, by the relationship:

$$\omega_\in(x)=f(\text{sign}(\langle \delta h(x,\delta x)\rangle_{|\delta x|=\in}))$$

where the function a→sign(a) is a sign function taking the value 1 if a is strictly positive, −1 if a is strictly negative, and 0 if a is zero, where the quantity $\delta h(x,\delta x)=h(x+\delta x)-h(x)$, and where the operator $\langle \delta h(x,\delta x)\rangle_{|\delta|=\in}$ returns an average value for the height differences for the set of pairs of points $\{x;x+\delta x\}$ of the topographical map such that the length $|\delta x|$ is substantially equal to the radius $\in$.

\* \* \* \* \*